United States Patent [19]

Odom

[11] 4,238,295
[45] Dec. 9, 1980

[54] ENERGY EFFICIENT RECOVERY OF ACRYLONITRILE

[75] Inventor: Paul S. Odom, Houston, Tex.

[73] Assignees: Standard Oil Company (Ohio) Cleveland, Ohio

[21] Appl. No.: 965,758

[22] Filed: Dec. 4, 1978

[51] Int. Cl.² ............................................. B01D 3/40
[52] U.S. Cl. ............................... 203/83; 203/DIG. 3; 203/96; 260/465.9
[58] Field of Search ..................... 203/DIG. 3, 95–97, 203/83, 76; 260/465.9, 465.1, 465.3

[56] References Cited

U.S. PATENT DOCUMENTS

| | | | |
|---|---|---|---|
| 3,073,753 | 1/1963 | Hadley et al. | 203/DIG. 3 |
| 3,328,266 | 6/1967 | Modiano et al. | 203/96 |
| 3,462,477 | 8/1969 | Caporali et al. | 260/465.9 |
| 3,936,360 | 2/1976 | Wu | 203/DIG. 3 |

Primary Examiner—Norman Yudkoff
Attorney, Agent, or Firm—David J. Untener; Herbert D. Knudsen; Larry William Evans

[57] ABSTRACT

Substantial operating cost savings are realized in the recovery of acrylonitrile from an aqueous solution containing acrylonitrile by using the recovery column bottoms stream to provide heat to one or more distillation columns in the process.

2 Claims, 1 Drawing Figure

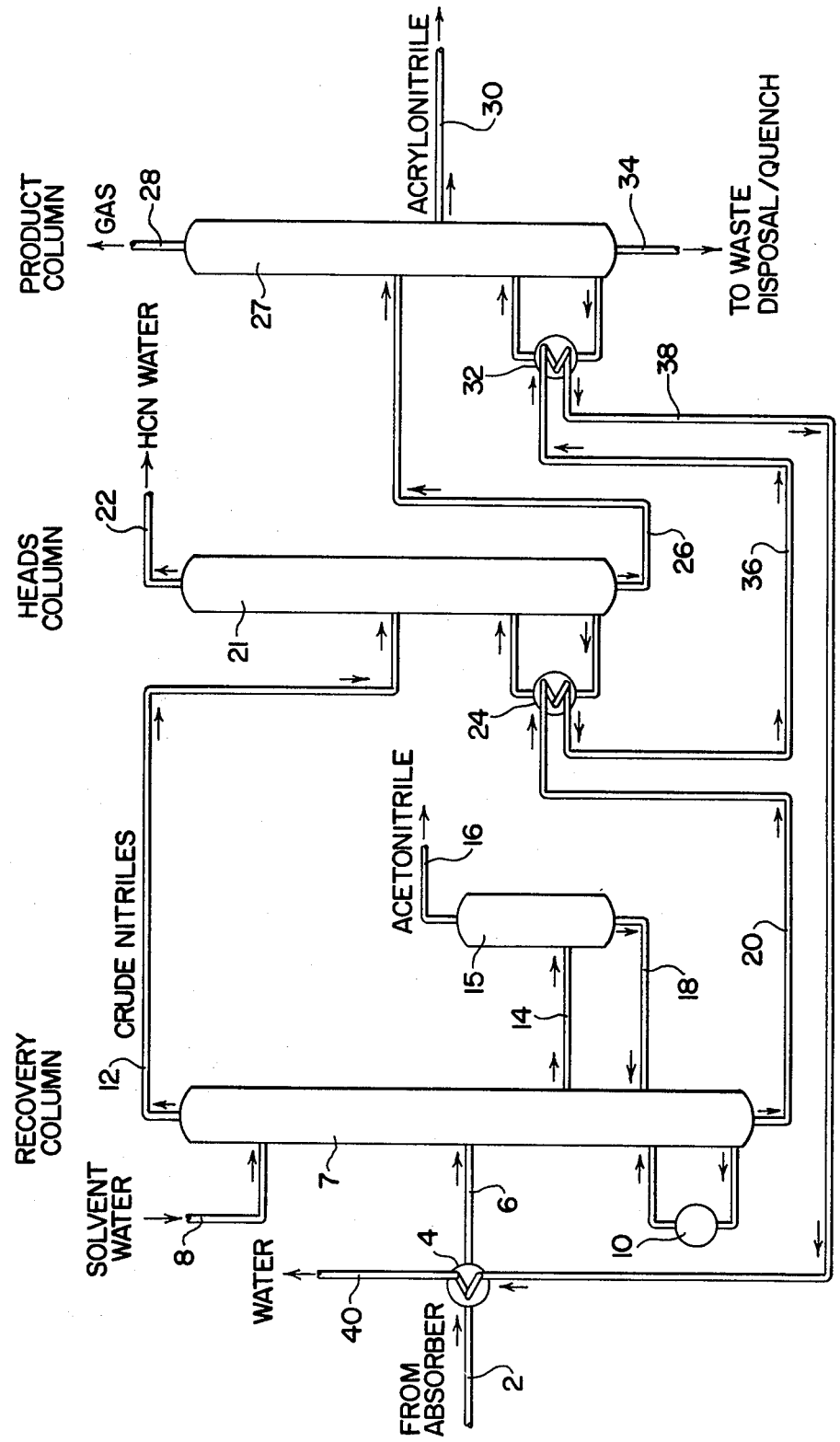

ENERGY EFFICIENT RECOVERY OF ACRYLONITRILE

BACKGROUND OF THE INVENTION

Recovery and purification systems for acrylonitrile are known, see for example U.S. Pat. Nos. 3,936,360; 3,433,822; and 3,399,120.

Typically, propylene, ammonia and air are reacted in a vapor phase with an ammoxidation catalyst. The vaporous reactor effluent is then passed to a quench system wherein the reactor effluent is directly contacted with an aqueous quenching liquid, usually water. This quenching removes unreacted ammonia and heavy polymers. The quenched gases then proceed to an absorption column.

In the absorber, the gases are directly contacted with an absorbing liquid, again usually water. The water, acrylonitrile, acetonitrile, HCN and associated impurities leave the bottom of the absorber in an aqueous solution. Inert gases are removed from the top of the absorber.

The aqueous solution then proceeds to a series of distillation columns to separate the respective components. The first of these is known as a recovery column. This column removes acetonitrile from the aqueous solution through extractive distillation. U.S. Pat. No. 3,399,120 to Lovett shows such a recovery column and its associated stripper. Improvements have been made in the prior art to the process of Lovett, such that acetonitrile is now removed as a sidestream from the recovery column.

U.S. Pat. No. 3,936,360 describes the common recovery scheme for further refining the overhead stream from the recovery column containing acrylonitrile, HCN, water and minor impurities. This stream is first passed to an HCN column with HCN being removed overhead; then to a drying column with water being removed overhead; and finally to a product column wherein product quality acrylonitrile is recovered. Improvements have also been made in this aspect of the process by combining the HCN and drying columns into one distillation column.

Associated with each of these columns is the requirement of heat addition to perform the necessary distillation. This heat addition is typically in the form of steam. The present invention greatly reduces the external steam requirements necessary to recover acrylonitrile, thereby substantially reducing the operating costs.

SUMMARY OF THE INVENTION

It has now been discovered that substantial reductions in external heat sources used in the process for the recovery and purification of acrylonitrile from an aqueous solution of acrylonitrile, acetonitrile, HCN in impurities can be obtained by the steps of:

(a) distilling said aqueous solution in an extractive distillation column with solvent water to produce overhead stream of acrylonitrile, HCN and water, and a bottoms stream of water and impurities;

(b) distilling the overhead stream of (a) in one or more additional distillation columns to recover product quality acrylonitrile, the improvement comprising passing said bottoms stream of (a) in indirect heat exchange relationship with one or more additional distillation columns to provide heat for distillation.

A preferred embodiment can be said to consist of the steps of:

(a) distilling said aqueous solution in an extractive distillation column with solvent water to produce an overhead stream of acrylonitrile, HCN and water, and a bottoms stream of water and impurities;

(b) distilling in a second distillation column the overhead stream of (a) to produce a second overhead stream of HCN and water, and a second bottoms stream of acrylonitrile and impurities;

(c) distilling in a product column the second bottoms stream of (b) to recover product-quality acrylonitrile, the improvement comprising; passing said bottoms stream of (a) in indirect heat exchange relationship with liquid from one or more distillation columns from steps (b) or (c) to provide heat to the respective distillation column.

The invention can best be understood by reference to the drawing.

DESCRIPTION OF THE DRAWING

The drawing is a schematic representation of an embodiment of the present invention in a typical acrylonitrile recovery process.

The aqueous solution from an absorber containing acrylonitrile, acetonitrile, HCN, water and impurities is passed through line 2 to exchanger 4, wherein the feed is preheated. The aqueous solution leaves the exchanger in line 6 and is passed to recovery column 7. Extractive distillation is performed in the recovery column with the addition of solvent water through line 8. Heat is supplied through exchanger 10 for the distillation. Three streams are removed from the recovery column. First, an overhead stream of acrylonitrile, HCN, water and some impurities is removed from the recovery column in line 12. A sidestream 14, is removed from the recovery column and passed to stripper 15 wherein acetonitrile is removed overhead in line 16, and the remaining liquid from the bottoms of the stripper is returned to the recovery column through line 18. Finally, a bottoms stream of water and some impurities is removed through line 20 whose use is the subject of the present invention, and will be discussed later.

Referring to the overhead line 12 from the recovery column, this overhead stream is passed to distillation column 21 which is in effect a column combining the operations of removing HCN and water. These are removed overhead through line 22. Heat is supplied to the distillation column through exchanger 24. And a liquid stream of acrylonitrile with minor amounts of water and impurities is removed from the bottoms of the column through line 26 and passed to product column 27.

Product column 27 serves to remove a specific portion of the remaining water and all of the various remaining impurities to obtain product specification acrylonitrile. Heat is applied to distillation column 27 through exchanger 32. The operation of this column varies in the prior art, but a typical embodiment is shown in the drawing wherein gases are removed overhead through line 28, acrylonitrile is removed as a sidestream through line 30, and the bottoms stream containing mostly water is removed through line 34 and passed to either waste disposal or the quench system, not shown.

Referring to the bottoms stream from recovery column 7, it can be seen how the present invention eliminates external heat requirements. Line 20 is first passed to exchanger 24 associated with the distillation column for removing HCN and water. After providing sufficient heat for this distillation, the liquid exits through line 36 to exchanger 32 which is used to provide sufficient heat for distillation in the product column. This stream then leaves exchanger 32 through line 38 and, as known in the prior art, exchanges heat in exchanger 4 with the feed to the recovery column. After exchanging heat, this stream through line 40 is then typically sent to the absorber as solvent water to recover acrylonitrile.

The present invention is applicable to any process for the recovery of acrylonitrile that has a recovery column and one or more additional distillation columns. The additional distillation columns typically consist of an HCN column, a drying column for removing water, and a product column for recovering the product-quality acrylonitrile. However, these separate operations may be combined as shown in the drawing wherein one distillation column removes both HCN and water. The operation of these columns are known in the art, the invention having no substantial impact on the operating parameters of the distillation columns.

The operation of the recovery column is also well known as shown in U.S. Pat. No. 3,399,120. This recovery column may consist of one extractive distillation column with sidestream removal of acetonitrile. Another embodiment, as shown in the Lovett reference, is to pass the bottoms of the recovery column to a separate stripping column wherein acetonitrile is removed overhead. The bottoms from this stripping column contains water and impurities. In this embodiment, the bottoms stream from this stripper is used as the heat source to provide heat to the additional distillation columns.

Although applicable to this above embodiment of a separate stripper column, the present invention will be discussed in terms of the embodiment shown in the drawings for ease of understanding. In the prior art, the recovery column bottoms has been used to preheat the incoming feed and then passed as solvent water to the absorber. The present invention greatly improves upon this by recovering the heat contained in this stream and using it to provide the necessary motivation for distillation.

As described in Ser. No. 535,402, the operation of the recovery column can be improved by using a lower solvent water temperature. In the prior art this solvent temperature has been between 140°–160° F. The above application describes an invention wherein recoveries are improved by reducing this solvent water temperature to below 140° F. without using external utilities. The use of lower solvent water temperature allows a great deal more heat to be removed from the recovery column bottoms than with the higher solvent water temperature, thus adding to the benefit of the present invention.

The specific sequence of distillation columns to be heated is important from an optimization point of view. Since the HCN-water column operates at a higher temperature than the product column, it is advantageous to first pass the recovery column bottoms stream to the HCN column, and then to the product column. Where there are separate columns for the removal of HCN and water, or where the operating temperatures of these columns are somewhat different, then the sequence will also be different. It is preferred that the recovery column bottoms stream exchange heat starting with distillation columns having the highest temperature in the process.

In a typical process for the recovery of acrylonitrile as shown in the drawing, external heat requirements to these columns can amount to 60,000 lbs/hr steam. By utilizing the present invention, this steam and its associated operating costs are greatly reduced, if not completely eliminated.

I claim:

1. In the process for the recovery and purification of acrylonitrile from an aqueous solution of acrylonitrile, acetonitrile, HCN and impurities consisting of the steps of:
   (a) distilling said aqueous solution in an extractive distillation column with solvent water to produce an overhead stream of acrylonitrile, HCN and water, and a bottoms stream of water and impurities;
   (b) distilling in a second distillation column the overhead stream of (a) to produce a second overhead stream of HCN and water, and a second bottoms stream of acrylonitrile and impurities;
   (c) distilling in a product column the second bottoms stream of (b) to recover product quality acrylonitrile, the improvement comprising; passing said bottoms stream of (a) in indirect heat exchange relationship with liquid from the second distillation column of (b) followed by the liquid from the product column of (c) to provide heat to the respective columns.

2. The process of claim 1 including the additional step of passing said bottoms stream of (a), after providing heat to said distillation columns, in indirect heat exchange relationship with the aqueous solution of step (a) prior to extractive distillation.

* * * * *